United States Patent [19]

Brown

[11] 4,256,437
[45] Mar. 17, 1981

[54] PERISTALTIC INFUSION PUMP AND METHOD

[75] Inventor: Fon R. Brown, Hyrum, Utah

[73] Assignee: Stewart Naumann Laboratories, Inc., Santa Clara, Calif.

[21] Appl. No.: 874,212

[22] Filed: Feb. 1, 1978

[51] Int. Cl.³ .................. F04B 49/06; A61M 5/00
[52] U.S. Cl. .................. 417/45; 128/214 E; 128/214 F; 417/63
[58] Field of Search .............. 417/45.63; 128/214 E, 128/214 F; 318/685, 696

[56] References Cited

U.S. PATENT DOCUMENTS

| | | | |
|---|---|---|---|
| 3,731,679 | 8/1973 | Wilhelmson | 128/214 E |
| 3,981,620 | 9/1976 | Abrahams et al. | 417/42 |
| 3,990,444 | 11/1976 | Vial | 128/214 F |
| 4,031,447 | 6/1977 | Fogo | 318/685 |
| 4,037,598 | 7/1977 | Georgl | 128/214 F |
| 4,081,736 | 3/1978 | Leenhouts | 318/685 |
| 4,107,593 | 8/1978 | Anderson | 318/685 |
| 4,114,144 | 9/1978 | Hyman | 128/214 E |
| 4,147,968 | 4/1979 | Goble | 318/696 |
| 4,155,362 | 5/1979 | Tess | 128/214 F |

FOREIGN PATENT DOCUMENTS 2379290  1/1978  France ............... 128/214 E

Primary Examiner—William L. Freeh
Attorney, Agent, or Firm—Flehr, Hohbach, Test

[57] ABSTRACT

A peristaltic infusion pump is disclosed herein and includes a continuous tubular arrangement adapted to pass intravenous fluids therethrough and a peristaltic pump head mounted for rotation about a fixed axis. This pump head includes a plurality of innerconnected, circumferentially spaced tube engaging members adapted to successively engage the tubular arrangement during rotation for peristaltically pumping fluid therethrough. In a preferred embodiment, the pump includes a stepping motor which is energized in a particular way for rotating the pump head and which is also used to sense occlusion in the tubular arrangement. This preferred pump also includes a particular arrangement for detecting the index of refraction of the intravenous fluid for detecting the presence of air bubbles or the like.

7 Claims, 5 Drawing Figures

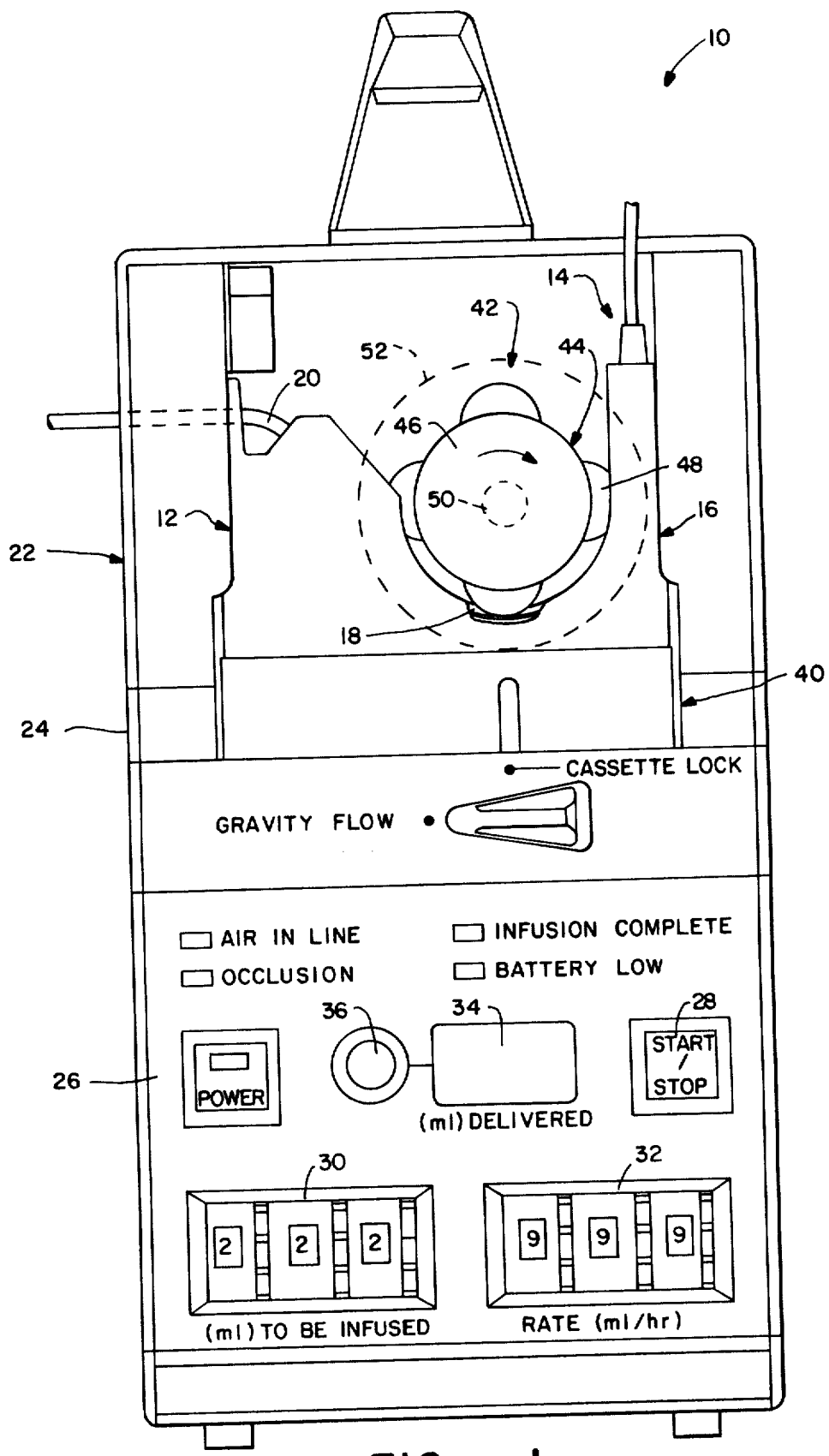
FIG.—1

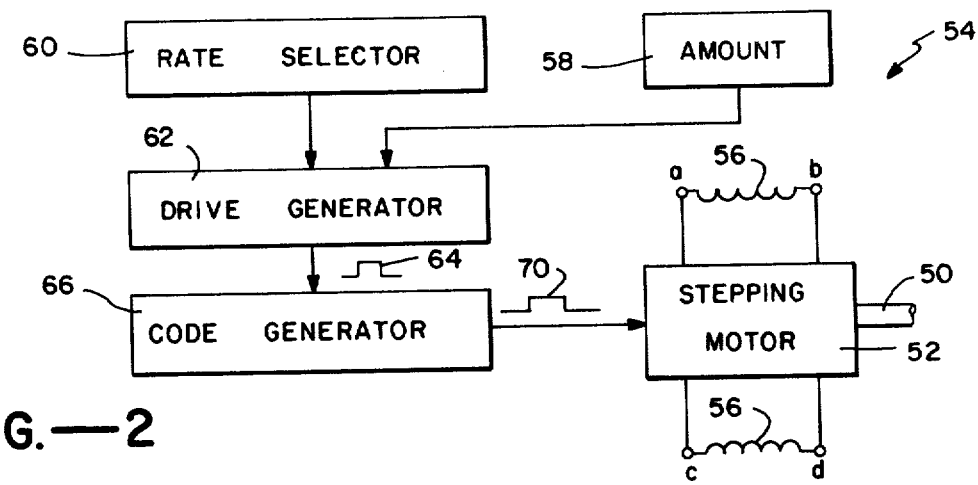
FIG.—2
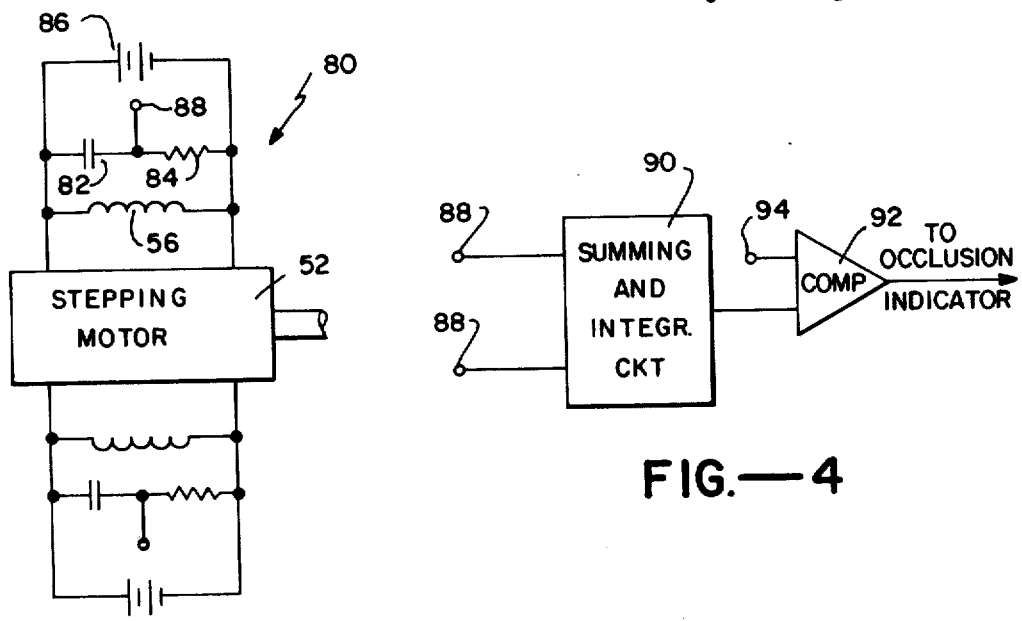
FIG.—3
FIG.—4
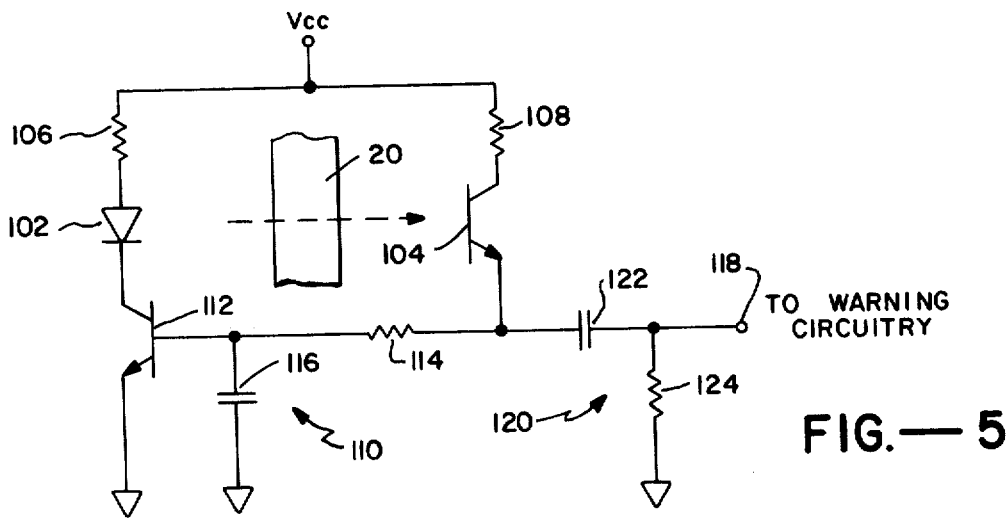
FIG.—5

PERISTALTIC INFUSION PUMP AND METHOD

BACKGROUND OF THE INVENTION

The present invention relates generally to infusion pumps for administering intravenous fluids and more particularly to specific features of a peristaltic infusion pump.

At the outset, reference is made to co-pending United States Patent application Ser. No. 868,525 entitled PERISTALTIC INFUSION PUMP AND DISPOSABLE CASSETTE FOR USE THEREWITH, filed on Jan. 11, 1978 now U.S. Pat. No. 4,187,057 and assigned to the assignee of the present application. This co-pending application discloses a specific type of peristaltic infusion pump comprising a disposable cassette and pump arrangement. The cassette includes a continuous tubular arrangement adapted to pass intravenous liquids therethrough and a cassette body for fixedly supporting a predetermined tubular section of the tubular arrangement in an exposed and readily accessible position. The pump arrangement includes structure for supporting the disposable cassette for movement between a first inoperative position and a second, spaced apart operative position and a pump head cooperating with the exposed and readily accessible section of the tubular arrangement when the cassette is in its operative position for peristaltically pumping fluid through the tubular arrangement.

In addition to the features just recited, the peristaltic pump described in this co-pending application includes a conventinal electrically energized motor for driving the pump head and it may include conventional means for sensing occlusion in the tubular arrangement during operation of the pump and conventional means sensing the index of refraction of the intravenous fluid as it passes through the tubular arrangement for detecting the presence of air bubbles or the like. As will be seen hereinafter, the present invention is directed to a peristaltic infusion pump utilizing a particular drive motor including an unconventional way to energize this motor, and unconventional approaches to detecting the presence of occlusions within the tubular arrangement and changes in the index of refraction of the intravenous fluid passing through this arrangement.

OBJECTS AND SUMMARY OF THE INVENTION

One object of the present invention is to provide an energy efficient peristaltic infusion pump provided for passing intravenous fluid through a tubular arrangement.

Another object of the present invention is to provide a peristaltic infusion pump including an uncomplicated and yet reliable approach for detecting an occlusion within the tubular arrangement during operation of the pump.

Yet another object of the present invention is to provide a peristaltic infusion pump which includes an uncomplicated and yet reliable approach to detecting any changes in the index of refraction of the intravenous fluid as it passes through the continuous tubular arrangement for detecting the presence of air bubbles or the like.

Many of the components making up the infusion pump disclosed herein may be identical to those discussed in the aforerecited co-pending application. In fact, as will be seen hereinafter, with certain exceptions relating to the specific aspects of the present invention, the peristaltic infusion pump disclosed herein may be identical to the pump disclosed in this co-pending application. As a result, this pump utilizes a continuous tubular arrangement which adapted to pass intravenous fluid therethrough and which includes a predetermined tubular section supported in an exposed and readily accessible position. A peristaltic pump head also comprising part of the pump is mounted for rotation about a fixed axis and includes a plurality of innerconnected, circumferentially spaced tube engaging members adapted to successively engage the exposed and readily accessible section of the tubular arrangement during rotation of the pump head for peristaltically pumping fluid therethrough.

In accordance with one aspect of the present invention, the pump head is rotated in incremental steps by means of an electromagnetic stepping motor having a fixed stator, a cooperating rotor, and an output shaft connecting the rotor with the pump head. This motor also includes electromagnetic coil means, specifically a plurality of coils which are subjected to successive predetermined current signals at spaced intervals in time for driving the rotor through successive circumferentially spaced magnetic detents, thereby rotating the pump head in incremental steps. However, in accordance with the present invention, these coils are maintained free of current during the intervals between the current signals, that is, between incremental steps of the pump head, which reduces energy consumption during operation of the infusion pump.

In accordance with another aspect of the present invention, a peristaltic infusion pump utilizing electromagnetic stepping motor means for rotating its pump head in incremental steps also includes means continuously sensing the load of the motor means during operation of the pump for sensing occlusion in its tubular arrangement. In a preferred embodiment, this is accomplished by sensing the back EMF across the coils during rotation of the drive head.

A peristaltic infusion pump of the general type described may also include means for detecting the index of refraction of the intravenous fluid passing through the tubular arrangement. This detecting means includes electrical light source means positioned on one side of the tubular arrangement for passing light therethrough, the magnitude of which, at any given time during operation of the pump, depends upon the index of refraction of the fluid passing through the arrangement. The detecting means also includes electrical light sensor means for sensing the light passed through the tubular arrangement and for producing an output signal corresponding to the magnitude of the light it senses. In accordance with still another aspect of the present invention, the magnitude of the light source is continuously maintained at a steady state level corresponding to the normal index of refraction of the particular intravenous fluid by means of a feed back circuit responsive to the output signal. In a preferred embodiment, this feed back circuit includes low pass filter means for blocking the passage of any abrupt and momentary changes in the output signal corresponding to an abrupt and momentary change in the index of refraction (for example an air bubble). In this way the magnitude of the light source is maintained at its steady state level corresponding to the normal index of refraction of the fluid regardless of the abrupt and momentary change in index of refraction.

BRIEF DESCRIPTION OF THE DRAWINGS

FIG. 1 is a front elevational view of an overall peristaltic pump assembly constructed in accordance with the present invention.

FIG. 2 is a block diagram illustrating an overall drive arrangement comprising part of the pump assembly illustrated in FIG. 1.

FIG. 3 schematically illustrates part of a circuit utilized for sensing occlusions in the pump assembly illustrated in FIG. 1.

FIG. 4 schematically illustrates a circuit comprising part of the occlusion detecting arrangement of FIG. 3.

FIG. 5 schematically illustrates a circuit arrangement for detecting changes in the index of refraction in intraveneous fluid which is pumped through a continuous tubular arrangement by means of the infusion pump illustrated in FIG. 1.

DETAILED DESCRIPTION AND PREFERRED EMBODIMENTS

Turning to the drawings, wherein like components are designated by like reference numerals throughout the various figures, attention is specifically directed to FIG. 1 which illustrates an overall peristaltic infusion pump assembly 10 constructed in accordance with the present invention. This overall assembly includes a disposable cassette 12 which, in the embodiment illustrated, is identical to the disposable cassette described in the previously recited co-pending application. Accordingly, a detailed description of this cassette will not be provided herein. It should suffice to say that the cassette includes a tubular arrangement 14 through which intravenous fluid is peristaltically pumped from a supply end (not shown) to the patient at its other end and a cassette body generally indicated at 16. Cassette body 16 is provided for supporting this tubular arrangement in position during operation of the pump assembly and particularly for supporting two predetermined tubular sections 18 and 20 in exposed and readily accessible positions.

Pump assembly 10 also includes a pump 22 which, with certain important exception to be discussed hereinafter, may be identical to the pump described in the previously recited co-pending application. Accordingly, pump 22 includes an overall housing 24 adapted to house and support the various components making up this pump. As illustrated in FIG. 1, this housing also includes a front panel 26 displaying a number of indicators including a start/stop button 28, a three digit thumb wheel 30 for setting the amount of intravenous (IV) fluid to be infused (in milliliters) and a three digit thumb wheel 32 provided for setting the rate of fluid to be infused (in milliliters/hours). This front panel also displays a number of other indicators which are selfevident from FIG. 1. These latter indicators include an AIR-IN-LINE indicator, an OCCLUSION indicator, a BATTERY LOW indicator, an INFUSION COMPLETE indicator and an arrangement 34 indicating the amount of fluid delivered at any point in time by depressing the associated button 36. These thumb wheels, indicators and the start/stop buttons will be discussed again briefly hereinafter.

In addition to the foregoing, as discussed in the co-pending application, pump 22 includes an arrangement 40 for supporting disposable cassette 10 for movement between a first inoperative position and a second spaced apart, locked operative position and it also includes an arrangement 42 utilizing a pump head 44 which cooperates with section 18 of tubular arrangement 16 when the cassette is in its operative position for peristaltically pumping IV fluid through the tubular arrangement.

In addition to these arrangements 40 and 42 (including pump head 44), the pump includes an arrangement which cooperates with previously recited section 20 of tubular arrangement 16 when the disposable cassette 10 is in its second operative position for automatically detecting any changes in the index of refraction of the IV fluid as the latter passes through section 20. It also includes an arrangement for detecting any occlusion in the tubular arrangement. With the exception of these latter two arrangements and the particular way in which pumping arrangement 116 is driven, pump 22 may be and preferably is identical to the pump described in the previously recited co-pending application. This includes conventional circuitry associated with the conventional components including for example conventional circuitry associated with the start/stop button 28, the two thumb wheels 30 and 32, the arrangement 34 and its associated actuating button 36 and the indicators INFUSION COMPLETE and BATTERY LOW. As will be seen, the circuitry associated with the indicators OCCLUSION and AIR-IN-LINE, form part of the present invention as does the scheme required for driving the pump associated arrangement 42 and will be discussed hereinafter.

As stated in the previously recited co-pending application, arrangement 42 utilizes a pump head 44 including a cylindrical housing 46 which supports a plurality of disc shaped, shaftless roller members 48 for free rotation about their own respective axes. The housing is fixedly mounted concentrically around one end of a central drive shaft 50 which has its otherwise free end mechanically coupled to (or comprises part of) the output of a motor 52 provided for driving the shaft and rotating the pump head. In this way, members 48 successively engage section 18 of tubular arrangement 16 for peristaltically pumping the IV fluid through the arrangement as described in the previously recited application.

In accordance with one aspect of the present invention, motor 52 is a conventional electromagnetic stepping motor having a fixed stator (not shown), a cooperating rotor (not shown), an output shaft connecting the rotor with pump head 44, specifically shaft 50, and a plurality of electromagnetic coils. This type of motor is well known to those in the art. As a result, it should suffice to say that the rotor is driven through successively circumferentially spaced magnetic detents as the electromagnetic coils are subjected to successive coded current signals. The amount of circumferential movement of the rotor during any given step and hence a total number of detents required for driving the rotor one revolution depends upon the motor design. In an actual working embodiment, stepping motor 52 is a 9 volt, 1.5 ampere stepping motor which is available from North American Phillips Control Corporation under Model No. K82932-MI. This particular motor moves 7.5 degrees per step and hence includes 48 detents through which the rotor must pass in making one revolution.

The type of electromagnetic stepping motor just described may be conventionally energized by subjecting its electromagnetic coils to successive coded current signals which drive the rotor from one detent to the next so long as the coils are subjected to the proper signals at the proper time, as is well known. However, it has been conventional practice to subject these coils to the proper current signals during movement of the rotor and but also during the quiescent period between rotor steps. This requires instantaneous changes in the coded signals, from one signal to the next, and it also means that the coils are continuously subjected to a current load whether the rotor is moving or not. As will be seen below, Applicant has found that this is not necessary when utilizing motor 52 for driving pump head 44 and, hence, the pump head utilizing less electrical energy.

Turning specifically to FIG. 2, attention is directed to an arrangement 54 for driving pump head 44. This arrangement includes previously described stepping motor 52 including shaft 50 and two electromagnetic coils generally designated at 56. The arrangement also includes a circuit arrangement 58 including the previously recited thumb wheel 32 for selecting the flow rate of IV fluid and a circuit arrangement 60 including previously recited thumb wheel 30 for selecting the total amount of IV fluid to be provided. As illustrated in FIG. 2, these two latter circuit arrangements have their output connected to the input of a drive generator 62 which produces successive output pulses or signals 64. These output signals are applied to the input of a code generator 66 which includes a power supply (not shown). As will be seen hereinafter, this latter component, that is, the code generator including its power supply is connected to the input of stepping motor 52 for operating the latter in the manner to be described. Inasmuch as the actual circuitry associated with each of the circuit arrangements 58 and 60 and each of the generators 62 and 64 may be conventional, these arrangements and generators have been represented in FIG. 2 by means of block diagrams. One with ordinary skill in the art can readily supply the detailed circuitry required to operate the arrangements and generators in the manner to be described.

In actual operation, the desired flow rate of the IV fluid, within predetermined limits, is set by thumb wheel 32 and the maximum amount to be provided is set by thumb wheel 30. The circuit arrangements 58 and 60 associated with these thumb wheels are connected to the input of drive generator 62 as stated above. As will be seen, the particular rate selected at the thumb wheel 32 determines the frequency of signals 64 produced at the output of drive generator 62 and the total amount of IV fluid selected by thumb wheel 30 determines the total number of of signals 64 which are generated during a particular period of operation of the overall pump. More specifically, as will be seen, motor 52 is stepped, that is, its rotor is moved from one detent to the next, for each signal 64. Accordingly, the frequency of this signal will determine the rate of rotation of the rotor and hence the rate of rotation of pump head 44. This rate of rotation, in turn, determines the rate at which the IV fluid is peristaltically pumped through tubular arrangement 14. Of course, the total number of signals will determine the total amount of rotation and hence the total amount of fluid pumped through the tubular arrangement.

The total width of each signal 64 is also important. The width should be selected to be of sufficient duration to assure that the rotor moves from one detent to the next and yet it should not be so long that it might cause the rotor to override an approaching detent. This is important because no current is to be provided to the motor during the period between its movements from detent to detent. More specifically, where current is provided between steps, the current is used to hold the rotor at its corresponding detent (between steps) until the next coded signal, as is well known. However, in the present invention, this "holding" current is eliminated and hence, it is necessary to limit the duration of the coded signal and hence signal 64 which is responsible for the coded signal, as will be seen. Where motor 50 is the particular stepping motor recited associated with an actual working embodiment as recited above, applicant has found that the signal 64 preferably varies in width between approximately 5 and 10 milliseconds depending upon the cassette load and type of tubing utilized in arrangement 14. However, those with ordinary skill in the art can readily provide the appropriate range depending upon the particular stepping motor used.

In response to and during the presence of signal 64, the code generator 66 produces a coded power initiating pulse 70 and a corresponding power pulse (not shown). This pulse will differ from one pulse to the next as dictated by the stepping motor specifications. Each pulse is applied to the input of the stepping motor so as to cause the two coils 56 to be subjected to current (power pulses) in a particular way. For example, where the motor's rotor is at a particular detent, for example a detent #1 (not shown), in order to move the rotor to the next detent, for example detent #2, a signal 70 which is referred to in Table I as $Q_1$ may cause the coils 56 to be subjected to current in the a-b and c-d directions, also indicated in Table I. In order to move the rotor to the next detent, the next signal 70, for example $\bar{Q}_1$ indicated in Table I causes the coils to be subjected to current in a different way for example in the b-a and c-d direction, depending upon the requirements of the motor. Table I sets forth five steps of the motor which are initiated by the coded signals $Q_1$, $\bar{Q}_1$, $Q_2$, $\bar{Q}_2$ which are repeated starting with in the fifth step.

TABLE I

| Step (Detent) | Code Signal (70) | Coil Current |
|---|---|---|
| 1 | $Q_1$ | a→b |
|   |   | c→d |
| 2 | $\bar{Q}_1$ | a←c |
|   |   | b→d |
| 3 | $Q_2$ | a←c |
|   |   | b←d |
| 4 | $\bar{Q}_2$ | a→c |
|   |   | b←d |
| 1 | $Q_1$ | a→c |
|   |   | b→d |

In accordance with one aspect of the present invention, as stated, the coded generator, actually its power supply, applies a power pulse across each of the coils only during the presence of coded signal 70 and maintains the coils free of current between pulses. This provides a more energy efficient drive arrangement.

Turning to FIGS. 3 and 4, attention is now directed to an arrangement 80 for sensing occlusion in tubular arrangement 14 during operation of pump assembly 10. This arrangement includes the previously described stepping motor 52 and its associated coils 56. As will be seen hereinafter, occlusion within the tubular arrangement is detected by sensing the load on the stepping motor by sensing the back EMF across each coil 56 during the period that pump head 44 moves one step. More specifically, where the tubular arrangement is clear, that this, where there is no occlusion present, the motor will operate at a relatively constant load level thereby producing a relatively constant back EMF. However, should the line become occluded, the motor load will increase, thereby reducing the back EMF across the coils. As will be seen below, this back EMF across each coil is measured indirectly to provide indication of the load across the motor which, in turn, provides an indication of occlusion.

As illustrated in FIG. 3, arrangement 80 includes a suitably sized charging capacitor 82 connected across each coil 56. A current limiting resistor 84 is connected in series with each of these capacitors and may be of a relatively small value, for example 3 ohms. A DC supply, for example a suitably sized battery, indicated at 86, is connected across each capacitor and associated resistor. The size of these capacitors and battery could be readily determined.

In operation, during the interval between steps of motor 52 (between signals 70) that is, during the period when the pump head is quiescent, each of the batteries 86 charges up its associated capacitor 82. As the motor steps, each of these capacitors discharges through its associated coil. The wave form across each of these capacitors during discharge is applied from an associated terminal 88 to the input of a conventional summing and integrating circuit 90 which is illustrated in FIG. 4. Circuit 90 adds and integrates the two signals at terminals 88 during discharge of the capacitors so as to provide a single output which is representative of the total energy discharged by the capacitors during the particular step. In this regard, the voltage discharged will drop further (deeper) and wider (longer) during the step when the motor is subjected to a heavier load than when it is subjected to a lighter load. Since occlusion in tubular arrangement 14 subjects motor 52 to a heavier load than if the arrangement were clear, the total energy signal at the output of circuit 90 will be greater during occlusion (period of heavy load) than under normal conditions when the arrangement is clear (during a lighter load). In order to detect an increase in energy and hence occlusion the output of circuit 90 is applied to a conventional comparator 92 having a reference input 94 connected to a reference signal (indicative of normal, nonocclusion operation), so that the two inputs can be continuously compared. Should the output of summing and integrating circuit 90 rise above the reference at 94 (indicating an occlusion), the comparator will automatically apply an indicating signal at its output. This latter output signal would be automatically applied to appropriate conventional cicuitry associated with the previously recited OCCLUSION indicator at the front panel 26 of the pump assembly for actuating the indicator.

Turning now to FIG. 5 attention is directed to an arrangement 100 provided for sensing the index of refraction of the intravenous fluid as the latter passes through section 20 of the tubular arrangement. This arrangement includes a light source, specifically a light emitting diode 102 (LED), and a light sensor, specifically a phototransistor 104, which are respectively connected on opposite sides of section 20 in the manner described in the previously recited co-pending application. As seen in FIG. 5, both the LED and phototransistor are respectively connected to a DC power supply, for example battery $V_{cc}$, through current limiting resistors 106 and 108. Arrangement 100 also includes a feedback circuit 110 which includes a PNP transistor 112 connected in circuit with the LED and a low pass filter comprising resistor 114 and capacitor 116 which are connected to the base of transistor 112. The output of arrangement 100, indicated generally a terminal 118 is connected to the output of phototransistor 104 (terminal 120) through a high pass filter comprising a capacitor 122 and resistor 124.

During normal operation of pump assembly 10 a particular IV fluid is passed through tubular arrangement 14 and specifically through section 20. The amount of light which passes through this fluid from the LED to the phototransistor will depend upon the normal, steady state index of refraction of the fluid. For example, if water is passed through the tube, most of the light will pass to the phototransistor whereas if blood is passed through, very little if any light will pass. In order to compensate for these differences between fluids, arrangement 100 includes feed-back circuit 110. In operation, as the fluid passes through section 100 at its normal index of refraction, the amount of light passing through the phototransistor is constant. This produces a fixed steady state signal at the phototransistor output 120 which is fed back to the base of transistor 112 through the low pass filter. This steady state signal of constant amplitude maintains the transistor at a particular conducting level. Accordingly, the brightness of the LED is maintained at a fixed level which ultimately depends on the normal index of refraction of the fluid. Note that this continuous signal from the output of the phototransistor is continuously passed to the base of transistor 112 by the low pass filter because the signal is relatively constant (low frequency).

Should there be an abrupt and momentary change in the index of refraction of the fluid, for example as a result of an air bubble or the like passing through section 20, the conduction level of the phototransistor will abruptly and momentarily change causing an abrupt and momentary change in its output signal, in the form of a pulse, at terminal 20. However, the low pass filter will block this abrupt pulse (indicative of a high frequency) from being applied to transistor 112. However, the pulse will be passed through the high pass filter 120 to the output 118 where it is applied through conventional circuitry to actuate the previously recited AIR-IN-LINE indicator. Note, that the high pass filter will not pass the normal and relatively steady state signal from the output of phototransistor 104.

From the foregoing, it should be apparent that during the operation of arrangement 100, so long as there is no change in the index of refraction of the fluid, the LED will be maintained at a level indicative of the normal index of refraction of the fluid and that no signal will exist at output 118. Upon detection of a change in the index of refraction, the abrupt signal or pulse will be applied to the output 118, but the signal will not be applied to transistor 112 and hence the intensity level of the LED will remain constant.

What is claimed is:
1. A peristaltic infusion pump comprising:
  (a) a continuous tubular arrangement adapted to pass intravenous fluids therethrough;
  (b) means for supporting a predetermined tubular section of said arrangement in an exposed and readily accessible position;
  (c) a peristaltic pump head mounted for rotation about a fixed axis, said pump head including a plurality of interconnected, circumferentially spaced tube engaging members adapted to successively engage said predetermined tubular section during rotation of said pump head for peristaltically pumping fluid through said tubular arrangement; and (d) means for rotating said pump head in incremental steps about said axis, said rotating means including electromagnetic stepping motor means; and (e) means sensing the load of said motor means during operation of said pump for sensing occlusion in said tubular arrangement.

2. A pump according to claim 1 wherein said stepping motor means includes a fixed stator, a cooperating rotor, an output shaft connecting said rotor with said pump head and electromagnetic coil means which, when subjected to successive predetermined current signals, drives said rotor through successive circumferentially spaced magnetic detents corresponding to said signals and wherein said occlusion sensing means includes means for sensing the energy level across said coil means and means for comparing said level to a reference level.

3. A pump according to claim 2 wherein said coil means includes a plurality of electromagnetic coils and wherein said energy sensing means includes a capacitor connected across each of said coils, means for charging each of said capacitors during the intervals between said signals, each of said capacitors discharging through its connected coil during said signals and means for sensing the energy across each of said coils during said discharge.

4. A pump according to claim 3 wherein said energy sensing means includes means for adding and integrating said energy across each of said coils and producing a signal indicative thereof.

5. A peristaltic infusion pump, comprising:
(a) a continuous tubular arrangement adapted to pass intravenous fluid therethrough;
(b) means for supporting first and second predetermined tubular sections of said arrangement in exposed and readily accessible positions,
(c) a peristaltic pump head mounted for rotation about a fixed axis, said pump head including a plurality of interconnected, circumferentially spaced tube engaging members adapted to successively engage said first predetermined tubular section during rotation of said pump head for peristaltically pumping fluid through said tubular arrangement;
(d) means for rotating said pump head about said axis; and
(e) means for detecting the index of refraction of said fluid as said fluid passes through said second tubular section, said detecting means including
  (i) electrical light source means positioned on one side of said tubular section for passing light therethrough, the amount of light passing through said second section at any given time during operation of said pump depending upon the index of refraction of fluid passing through said second section,
  (ii) electrical light sensor means positioned on the other side of said second tubular section for sensing said passed light and producing an output signal corresponding to the amount of said passed light,
  (iii) feedback means responsive to said output signal and connected with said light source means for maintaining the magnitude of said light source means at a level corresponding to the index of refraction of said fluid, said feedback means including low pass filter means for preventing passage of any abrupt momentary changes in said output signal from effecting the intensity of said light source means, whereby the magnitude of said light source means is maintained at a steady state level corresponding to the normal index of refraction of said fluid, and
  (iv) means responsive to said abrupt and momentary changes in said output signal for producing a warning signal at a predetermined terminal point in response thereto, said last-mentioned means including high pass filter means for preventing said output signal from causing the production of said warning signal at said terminal point when said output signal corresponds to a steady state index of refraction of said fluid.

6. A pump according to claim 5 wherein said feedback means includes low pass filter means blocking the passage of any abrupt momentary changes in said output signal, whereby the magnitude of said light source is maintained at a steady state level corresponding to the normal index of refraction of said fluid.

7. A pump according to claim 6 wherein said detecting means includes means responsive to said abrupt and momentary changes in said output signal for producing a warning signal in response thereto, said last-mentioned means including high pass filter means blocking the passage of said output signal when the latter corresponds to a steady state index of refraction of said fluid.

* * * * *